United States Patent [19] [11] 4,282,167
Sy et al. [45] Aug. 4, 1981

[54] CONVERSION OF AMIDES TO ISOCYANATES VIA PHASE TRANSFER CATALYSIS

[75] Inventors: Anita O. Sy; Joseph W. Raksis, both of Columbia, Md.

[73] Assignee: W. R. Grace & Co., New York, N.Y.

[21] Appl. No.: 112,649

[22] Filed: Jan. 16, 1980

[51] Int. Cl.³ ............................................. C07C 118/04
[52] U.S. Cl. .................................................. 260/453 P
[58] Field of Search ...................................... 260/453 P

[56] References Cited

U.S. PATENT DOCUMENTS

| | | | |
|---|---|---|---|
| 2,640,846 | 6/1953 | Hurwitz et al. | 260/453 P |
| 3,277,140 | 10/1966 | Donovan et al. | 260/453 P |
| 3,465,025 | 9/1969 | Brownstein et al. | 260/453 P |
| 3,483,242 | 12/1969 | Brownstein et al. | 260/453 P |
| 3,523,962 | 8/1970 | Ottmann et al. | 260/453 PC |
| 3,707,495 | 12/1972 | MacRay et al. | 260/453 P |
| 3,873,589 | 3/1975 | Coury et al. | 260/453 SP |

OTHER PUBLICATIONS

Lee et al., Tetrahedron Letters, No. 20, pp. 1641–1644 (1976).
Wallis et al., Organic Reactions, John Wiley and Sons, Inc., New York, p. 267 (1949).
Morrison and Boyd, Organic Chemistry, Allyn and Bacon, Boston, 1960, p. 536.

Primary Examiner—Dolph H. Torrence
Attorney, Agent, or Firm—Philip M. Pippenger

[57] ABSTRACT

The present invention is a method of subjecting amides to a modified Hofmann reaction using a 2-phase aqueous/organic system. The Hofmann reaction is modified in the sense that the product is an organic isocyanate rather than an amine. Generally, the reaction employs a phase transfer catalyst although, for tertiary amides it has been discovered that use of the catalyst is not required.

21 Claims, No Drawings

CONVERSION OF AMIDES TO ISOCYANATES VIA PHASE TRANSFER CATALYSIS

BACKGROUND OF THE INVENTION

Phase transfer catalysis is a relatively recent technique which has been employed in a number of organic reactions which proceed via displacement of a leaving group by a nucleophile. Phase transfer catalysis utilizing a quaternary salt (e.g., ammonium, phosphonium or arsonium) as the phase transfer catalyst (i.e. PTC) is believed to work in the following way. In general, there are two immiscible phases. One of these phases (usually aqueous) contains a reservoir of a salt expected (e.g., a hypobromite salt) to function either as a base or nucleophile. The second phase is organic and contains the substrate which is expected to react with the salt. Because the salt-containing phase is insoluble in the substrate-containing phase, there will be no reaction observed in the absence of interfacial phenomena. A phase transfer catalyst is added to the mixture. This is ordinarily a quaternary ammonium or phosphonium halide or bisulfate which contains a lipophilic cation. The lipophilic cation enjoys solubility in both aqueous and organic phases and when in contact with the aqueous reservoir of salt proceeds to transport the nucleophile into the organic phase where reaction with the substrate is possible.

A journal article by Lee and Freedman (Tetrahedron Letters No. 20, pp 1641–1644, 1976) describes oxidation of various substrates to form amines using a phase transfer catalyst. This article mentions (page 1643) that when amides are subjected to phase transfer catalysis using PTC/hypochlorite, the resulting Hofmann rearrangement and oxidation of the amine product yields nitriles, aldehydes or ketones depending on the amide starting material employed.

British Pat. No. 1,384,157 describes the use of phase transfer catalysis to convert acyl halides to the corresponding acyl azides which are then converted (via Curtius Rearrangement) to the isocyanate. Aliphatic isocyanates, such as those prepared by the process of the invention, have also frequently been prepared by phosgenation of amines and dehydrohalogenation of the resulting carbamoyl chloride. See S. Ozaki, Chem. Revs., 72, 457 (1972); Saunders et al., Chem Revs., 43, 203–18 (1978); and Arnold et al., Chem. Revs., 57, 47–76 (1957).

It is also known that isocyanates are formed under the usual conditions of the Hofmann reaction, but such isocyanates are readily hydrolyzed to the corresponding amine. See Wallis et al., The Hofmann Reaction, Organic Reactions, John Wiley & Sons, Inc., New York, 1949, page 267. However, when the Hofmann reaction is carried out in the absence of water, it has been possible to isolate an isocyanate. See Morrison and Boyd, Organic Chemistry, Allyn and Bacon, Boston, 1960, page 536.

DESCRIPTION OF THE INVENTION

The present invention is a process for the preparation of an organic isocyanate (e.g., aliphatic isocyanate) which comprises contacting a solution of a substantially water-insoluble organic amide (e.g., an alicyclic or aliphatic amide) with an alkali metal hypobromite and a quaternary salt as phase transfer catalyst. The amide is dissolved in a substantially water-immiscible organic solvent. A sufficient amount of water is employed to allow interchange by the hypobromite anion and the anion of the quaternary salt. As a result of the phase transfer catalyst, an organic isocyanate corresponding to the amide employed, is formed in the organic phase.

With reference to the organic solvent, the term water-immiscible means that the solvent solubility in water is less than 50% (and preferably less than 10%) by weight at ambient room temperatures. The amide is considered to be water insoluble if its solubility is less than 50% (and preferably less than 10%) by weight at ambient room temperature. At ambient room temperature the solubility of the phase transfer catalyst in the aqueous reaction phase should be at least 0.0001 molar and solubility in the organic phase should be at least 0.0001 molar. Preferably, catalyst solubility in the organic phase exceeds solubility in the aqueous phase.

The organic amides employed are aliphatic rather than aromatic, i.e., the carbonyl carbon of the atom is not attached directly to an aromatic ring or an aralkyl group (e.g., benzyl or beta-phenylethyl can be employed). Of the aliphatic amides, the secondary amides are preferred. By "secondary" it is meant that the alpha carbon atom of the amide is attached to two alkyl groups. Similarly, by "primary" it is meant that the alpha carbon atom is attached to only a single alkyl group. An example of a secondary amide is cyclohexyl amide whereas n-heptanoyl amide is an example of a primary amide.

Where primary amides are employed it has been found desirable to use a more dilute reaction mixture than is employed with secondary amides; e.g., a concentration of the amide in the organic phase of from 0.4 molar to 2.5 molar is satisfactory for secondary amides. It is desirable to use a concentration of from 0.15 molar up to about 2.5 molar for primary amides. Regardless of the type of amide employed, the initial concentration should be at least 0.05 molar.

Amides useful in the present invention are exemplified by those having the following formula:

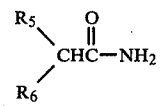

wherein $R_5$ and $R_6$ independently are hydrogen or an aliphatic or alicyclic group containing from 1 to 10 carbons, provided that the total number of carbons in $R_5$ and $R_6$ combined is sufficient to render the amide substantially insoluble in the aqueous phase of the reaction mixture. Alternatively, $R_5$ and $R_6$ taken together with the alpha carbon atom of the amide can be a cycloaliphatic group containing from 6 to 8 carbon atoms. In the above formula it can be seen that where either $R_5$ or $R_6$ is hydrogen the amide is primary, and where both $R_5$ and $R_6$ are alkyl groups the amide is secondary. The $R_5$ and $R_6$ groups should not be substituted by electron-withdrawing groups such as oxygen. Additionally, the amide should contain only a single amide nitrogen.

Suitable primary amides include: 2-norbornaneacetamide, n-octanoyl amide, n-heptanoyl amide and cyclohexanepropionamide. Suitable secondary amides include: cyclohexyl amide, cycloheptylamide, 2-norbornylcarboxamide and 2-ethylhexanoylamide. A tertiary amide useful in the present invention is 1-methylcyclohexylamide.

The N-halo amides (e.g., N-bromo and N-chloro) appear to be equivalent to the amides discussed above. The N-bromo amide is believed to be an intermediate in the Hofmann reaction. Accordingly, use of the N-bromo compound is essentially equivalent to reacting the unsubstituted amide with hypobromite. Additionally, as demonstrated in the Examples, the N-chloro amide can be converted to the corresponding isocyanate.

The secondary and tertiary amides can be employed without a phase transfer catalyst. For secondary amides the yields are markedly improved (e.g. by 50% of more) if a phase transfer catalyst is employed. For tertiary amides the yields without a phase transfer catalyst are essentially equivalent to yields obtained when a catalyst is employed.

In carrying out the process of the invention the order in which the reactants are admixed is not critical. Generally, the amide (carried in the organic solvent phase) is added to the aqueous hypobromite solution. Conveniently, the hypobromite is formed in situ by reaction of bromine with a base e.g., NaOH or KOH, in the presence of water previously added.

In carrying out the reaction, the initial (i.e., at the start of the reaction) amide concentration in the organic phase is from 5 to 30 weight percent, based on the weight of the organic solvent. The initial molar catalyst/amide ratio is from 0.05 to 10. The initial molar alkali metal hydroxide/amide ratio is from 1 to 13.

While the amount of water employed must be sufficient to allow the hypobromite ion to be formed—e.g., by solubilization of a hypobromite salt or reaction of bromine with an alkali metal hydroxide—preferably the volumetric ratio of the aqueous to the organic phase is from 0.5 to 1. The amount of water employed should also be sufficient to solubilize the phase transfer catalyst. If sufficient water is present, as described above, the hypobromite ion will exchange with the anion of the phase transfer catalyst and cause conversion in the organic phase of the amide to the corresponding isocyanate.

Suitable water-immiscible organic solvents include aliphatic, alicyclic or aromatic hydrocarbons or chlorinated hydrocarbons such as methylene chloride, heptane, cyclohexane, toluene, benzene, and chlorobenzene. Additionally, ethers and esters can also be employed as solvents provided they have the requisite solubility characteristics and are not reactive with the isocyanate product.

The process of the invention does not require heating and is generally conducted at room temperature. However, the process can be conducted at temperatures as low as 5° C. and as high as 30° C. The upper limit on temperature is dictated only by the fact that disadvantageous side reactions occur to an unreasonable extent. At the lower end of the temperature range reaction times tend to be lengthened. The reaction, as measured from the time of initial admixture of the reactants, is generally from 10 to 30 minutes although, longer and shorter times can be employed if desired. It has been found that at room temperature the yield of isocyanate decreases (depending upon the isocyanate present) after a certain point (e.g., 15–30 minutes) due to side reactions involving the isocyanate group. The reaction time can be extended by using lower reaction temperatures. For particular isocyanates, the reaction time to obtain optimum yields can easily be determined by routine experimentation. Similarly, to determine an optimum temperature several runs will be necessary.

Phase transfer catalysts useful in the invention are quaternary salts having the formula:

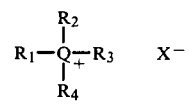

wherein the total number of carbon atoms in $R_1$, $R_2$, $R_3$ and $R_4$ is sufficient to render the catalyst soluble in both the organic and aqueous phases and wherein Q is nitrogen, phosphorous or arsenic. The average number of carbon atoms in the R groups of the catalyst is from 1 to 12 and the total number of carbons in the R groups is from 4 to 30. When using an ammonium quaternary catalyst it is preferred that the total number of carbons range from 10 to 30 and average from 16 to 20.

In describing the catalysts it will be understood that the catalyst is generally employed as the chloride, bromide or bisulfate salt of the quaternary cation, i.e., X is chloride, bromide, bisulfate or any other anion inert to the reactants and which will exchange with the hypobromite anion. The actual phase transfer catalyst is believed to be the quaternary cation which associates with the hypobromite anion and which is believed to "transfer" this anion to the organic phase where reaction occurs. Obviously, a quaternary hypobromite salt can be employed if available.

In selecting a cation in conformity with the above specifications, $R_1$, $R_2$, $R_3$ and $R_4$ can independently be hydrogen or an aliphatic, alicyclic or aromatic group containing from 1 to 18 carbon atoms as exemplified by methyl, ethyl, propyl, butyl, pentyl, hexyl, heptyl, octyl, nonyl, decyl, undecyl, dodecyl, hexadecyl, heptadecyl, octadecyl and benzyl.

Suitable phase transfer catalysts include: trioctyl methyl ammonium bromide, benzyl triethyl ammonium bromide, hexadicyltrimethyl ammonium bromide, trioctyl ethyl ammonium bromide, hexyl triethyl ammonium bromide, hexadienyl triethyl ammonium bromide, dodecyl triethyl ammonium bromide, tridodecyl methyl ammonium chloride, didodecyl dimethyl ammonium chloride, trimethyl dodecyl ammonium chloride, tridodecyl pentyl ammonium bromide, trihexyl hexadecyl ammonium bromide, triiododecyl benzyl ammonium chloride, trimethyl benzyl ammonium chloride, tetrabutyl phosphonium chloride, trioctyl ethyl phosphonium bromide, triethyl hexadecyl phosphonium bromide, hexadecyl tributyl phosphonium bromide, tributyl decyl phosphonium bromide, tetraphenyl phosphonium bromide and chloride and tetraphenyl arsonium chloride.

EXAMPLES 1–13

Various amides were converted to their corresponding organic isocyanates using tetrabutyl ammonium bisulfate as the phase transfer catalyst. The reaction was carried out by dissolving 0.5 grams of sodium hydroxide in 1 ml of water and adding 1.5 grams of ice to cool the solution to approximately room temperature. Subsequently, 2 milliequivalents of bromine were added followed by 2.6 ml of methylene chloride, 5 mole percent (based on the amide) of the phase transfer catalyst and 1.163 millimoles of the amide. The above materials were allowed to react at about room temperature for 15–20 minutes with agitation to intimately admix the organic and aqueous phases. Following the reaction period, the organic and aqueous phases were allowed to separate and the methylene chloride phase was extracted with a pipette. In some instances several milliliters of water were added to achieve distinct phase separation so that the methylene chloride layer could be more easily separated from the aqueous phase.

Following separation, the water phase was extracted several times with 5–10 ml of fresh methylene chloride and the methylene chloride extracts were combined and extracted once with water. Subsequently, the methylene chloride phase was dried with sodium sulfate and the methylene chloride was removed by distillation. The yield of isocyanate was determined by gas chromatography (dodecane std.). The amides employed, as well as the yields of isocyanate are presented in Table I below. In each Example the catalyst was tetrabutyl ammonium hydrogen sulfate which was converted to the hypobromite salt in situ.

TABLE I

| Example | Amide | Yield (%-based on amide) |
|---|---|---|
| 1 | (n-$C_6H_{13}$)-$CONH_2$ | 23% |
| 2 | (n-$C_6H_{13}$)-$CONH_2$ | 46% (5 minute reaction time) |
| 3 | (n-$C_6H_{13}$)-$CONH_2$ | 3.4% (no catalyst) |
| 4 | (n-$C_7H_{15}$)-$CONH_2$ | 19% |
| 5 | ⌬-$CH_2CH_2CONH_2$[1] | 16% |
| 6 | $CH_3$-⌬-$C(CH_3)_2$-$OCH_2CONH_2$ | 0% |
| 7 | (norbornyl)-$CH_2CONH_2$[1] | 26% |
| 8 | (norbornyl)-C(=O)-$NH_2$ | 48% |
| 9 | $H_3C$\\$CHCH_2CH$/$CH_3$ with $H_3C$/ and \\$OCH_2CH_2CONH_2$ | 0% |
| 10 | $NH_2C$(=O)-⌬-$C$(=O)$NH_2$ | 0% |
| 11 | ⌬-$CONH_2$ | 56% |
| 12 | ⌬($CH_3$)($CONH_2$) | 96% |
| 13 | (F-⌬)-C(=O)-$NH_2$ | 87% |

[1] It should be noted that the yields in Examples 5 and 7 increased to 86% and 87% respectively upon dilution, i.e., 1.2 mmoles of amide, 2 meq. $Br_2$, 13 meq. of NaOH, 26 ml. $CH_2Cl_2$, 25 ml. $H_2O$ and 5 mmole % PTC.

EXAMPLES 14–24

Proceeding as in Examples 1–13, various amides were converted to the corresponding aliphatic isocyanates using a number of different phase transfer catalysts. The amides employed along with the PTC's and yields are set forth in Table II below. Following the Table is a key identifying the abbreviations for the catalysts employed.

TABLE II

| Example | Amide | PTC | Yield (%-based on amide) |
|---|---|---|---|
| 14 | (n-$C_6H_{13}$)-$CONH_2$ | $PTC_1$ | 8.2% |
| 15 | (n-$C_6H_{13}$)-$CONH_2$ | $PTC_1$ | 15% |
| 16 | (n-$C_6H_{13}$)-$CONH_2$ | $PTC_1$ (used 50 mg) | 20% |
| 17 | (n-$C_6H_{13}$)-$CONH_2$ | $PTC_2$ | 6.2% |
| 18 | (n-$C_6H_{13}$)-$CONH_2$ | $PTC_2$ | 6% |
| 19 | (n-$C_6H_{13}$)-$CONH_2$ | $PTC_3$ | 18% |
| 20 | (n-$C_6H_{13}$)-$CONH_2$ | $PTC_4$ | 23% |
| 21 | ⌬-$CONH_2$ | $PTC_4$ | 81% |

TABLE II-continued

| Example | Amide | PTC | Yield (%-based on amide) |
|---|---|---|---|
| 22 | 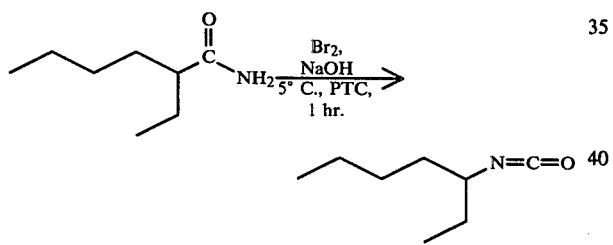 | PTC$_4$ | 26% |
| 23 | | PTC$_4$ | 10% (estimated) |
| 24 | 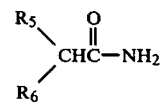 | none | 90% |

PTC$_1$ = hexadecyltrimethyl ammonium bromide
PTC$_2$ = tetramethyl ammonium chloride
PTC$_3$ = benzyltriethyl ammonium chloride
PTC$_4$ = tetrabutyl phosphonium bromide

EXAMPLE 25 CONVERSION OF 2-ETHYL HEXANOYL AMIDE (EHA)

EHA was prepared by treating 2-ethyl hexanoic acid with thionyl chloride followed by cold ammonium hydroxide. The resulting amide was reacted as in Examples 1–13 with the exception that the reaction time was 1 hour and the temperature was about 5° C. The yield was 80% based on the starting amide. When the reaction was carried out at 25° C. for 10–15 minutes similar yields were obtained. When no PTC was employed the yield was 55–70%. When the reaction was carried out at 5° C. with no phase transfer catalyst, the yield was 20–30%. The reaction can be depicted as follows:

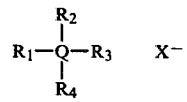

EXAMPLE 26 CONVERSION OF N-CHLOROCYCLOHEXYL AMIDE (CCA)

To 100 mg (0.62 mmole) of CCA dissolved in 2.2 ml of methylene chloride was added 0.6 ml of 5% aqueous NaOH, 1.6 ml of water and 11 mg of tetra-n-butyl ammonium bisulfate. The mixture was stirred at room temperature for 10 minutes and the layers separated. The organic layer was dried and concentrated to give 69% yield of cyclohexyl isocyanate as determined by GC analysis.

What is claimed is:

1. A process for the preparation of an organic isocyanate which comprises contacting a solution of a substantially water-insoluble aliphatic or cycloaliphatic organic amide in a substantially water-immiscible organic solvent, with an alkali metal hypobromite and a quaternary salt as phase transfer catalyst and a sufficient amount of water to form a continuous or discontinuous aqueous phase and form an organic isocyanate in the organic phase.

2. A process as in claim 1 wherein the organic solvent is an aliphatic, alicyclic or aromatic hydrocarbon or a halogenated hydrocarbon.

3. A process as in claim 1 where the initial concentration of the amide in the organic phase is at least 0.05 molar.

4. A process as in claim 1 wherein the initial molar catalyst/amide ratio is from 0.05 to 10.

5. A process as in claim 1 wherein the alkali metal hypobromite is formed directly in the aqueous phase by reacting bromine with sodium hydroxide or potassium hydroxide.

6. A process as in claim 5 wherein the molar ratio of alkali metal hydroxide/amide ranges from about 1 to about 13.

7. A process as in claim 1 wherein sufficient water is employed to form a solution of the quaternary salt.

8. A process as in claim 1 wherein the phase transfer catalyst is a quaternary salt having the formula:

$$R_1 - Q - R_3 \quad X^-$$
with $R_2$ above and $R_4$ below Q wherein the total number of carbon atoms in $R_1$, $R_2$, $R_3$ and $R_4$ is from 4 to 30, and $R_1$, $R_2$, $R_3$, and $R_4$ each contains from 1 to 12 carbons, and wherein Q is nitrogen, phosphorous or arsenic.

9. A process as in claim 8 wherein the catalyst is a quaternary ammonium salt.

10. A process as in claim 8 wherein the catalyst is selected from the group consisting of tetrabutyl ammonium bromide, hexadecyltrimethyl ammonium bromide, tetramethyl ammonium chloride, benzyltriethyl ammonium chloride and tetrabutyl phosphonium bromide.

11. A process as in claim 1 wherein the amide has the formula:

$$\begin{array}{c} R_5 \\ \phantom{R}\diagdown \\ \phantom{RR}CHC-NH_2 \\ \phantom{R}\diagup \phantom{CC}\| \\ R_6 \phantom{CCCC} O \end{array}$$

wherein $R_5$ and $R_6$ independently are hydrogen or an aliphatic or alicyclic group containing from 1 to 10 carbons, provided that the total number of carbons in $R_5$ and $R_6$ combined must be sufficient to render the amide substantially insoluble in the aqueous phase; or wherein $R_5$ and $R_6$ taken together with the alpha carbon atom form a cycloaliphatic group containing from 6 to 8 carbon atoms.

12. A process as in claim 11 wherein neither $R_5$ or $R_6$ is hydrogen and the amide is a secondary amide.

13. A process as in claim 11 wherein the amide has the following formula:

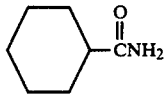

14. A process as in claim 11 wherein the amide has the following formula:

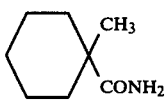

15. A process as in claim 11 wherein the amide has the following formula:

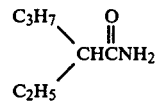

16. A process as in claim 11 wherein the amide has the following formula:

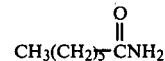

17. A process as in claim 11 wherein the amide has the following formula:

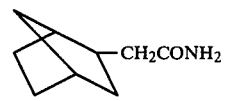

18. A process for the preparation of an organic isocyanate which comprises contacting a solution of a substantially water-insoluble aliphatic or cycloaliphatic N-halo organic amide in a substantially water-immiscible organic solvent, with an alkali metal hypobromite and a quaternary salt as phase transfer catalyst and a sufficient amount of water to form an organic isocyanate in the organic phase.

19. A process as in claim 18 wherein the amide is the N-chloro amide.

20. A process for the preparation of an organic isocyanate which comprises contacting a solution of a substantially water-insoluble aliphatic or cycloaliphatic secondary or tertiary organic amide in a substantially water-immiscible organic solvent with an alkali metal hypobromite and a sufficient amount of water to form an organic isocyanate in the organic phase.

21. A process as in claim 20 wherein the amide is a tertiary amide.

* * * * *